United States Patent
Peters

(10) Patent No.: US 9,504,783 B2
(45) Date of Patent: Nov. 29, 2016

(54) FLUID INTERCONNECTION SET WITH PARTICLE FILTER

(76) Inventor: Jean-Pierre Peters, Hasselt (BE)

(*) Notice: Subject to any disclaimer, the term of this patent is extended or adjusted under 35 U.S.C. 154(b) by 934 days.

(21) Appl. No.: 13/487,845

(22) Filed: Jun. 4, 2012

(65) Prior Publication Data

US 2012/0310082 A1 Dec. 6, 2012

Related U.S. Application Data

(63) Continuation-in-part of application No. PCT/EP2009/066383, filed on Dec. 3, 2009.

(51) Int. Cl.
| | | |
|---|---|---|
| *A61B 6/00* | (2006.01) | |
| *A61M 5/00* | (2006.01) | |
| *A61M 5/142* | (2006.01) | |
| *A61M 5/165* | (2006.01) | |

(52) U.S. Cl.
CPC ......... *A61M 5/007* (2013.01); *A61M 5/14216* (2013.01); *A61M 5/165* (2013.01); *A61M 2205/7545* (2013.01); *A61M 2205/7563* (2013.01)

(58) Field of Classification Search
USPC ...................................... 600/431; 604/80–58
See application file for complete search history.

(56) References Cited

U.S. PATENT DOCUMENTS

| 4,573,967 A * | 3/1986 | Hargrove et al. ............... 604/85 |
| 4,664,650 A * | 5/1987 | Urquhart et al. ............... 604/85 |
| 5,843,037 A * | 12/1998 | Uber, III ........................ 604/151 |
| 5,860,957 A * | 1/1999 | Jacobsen et al. ............ 604/156 |
| 6,056,727 A | 5/2000 | O'Neil |
| 2003/0120204 A1 * | 6/2003 | Unger et al. .................... 604/82 |
| 2005/0113754 A1 * | 5/2005 | Cowan ........................... 604/131 |

FOREIGN PATENT DOCUMENTS

| EP | 1 726 328 A1 | 11/2006 |
| GB | 1297794 A | 11/1972 |
| WO | 93/00944 A1 | 1/1993 |

OTHER PUBLICATIONS

International Search Report for Entry of PCT/EP2009/066383 dated Aug. 18, 2010.

* cited by examiner

*Primary Examiner* — Joel F Brutus
(74) *Attorney, Agent, or Firm* — Sughrue Mion, PLLC

(57) ABSTRACT

A fluid dispensing system 3 for dispensing one or more fluids from one or more reservoirs 2 to a patient, the fluid dispensing system comprising a particle filter 13 for preventing particles of a size larger than a predetermined size from being injected into the patient. The invention also relates to a reusable interconnection set 1 comprising a particle filter 13 for use in such a fluid dispensing system 3. The invention also relates to the use of such a fluid dispensing system 3 or reusable interconnection set 1 for dispensing a fluid or contrast fluid to a patient.

15 Claims, 7 Drawing Sheets

# FLUID INTERCONNECTION SET WITH PARTICLE FILTER

FIELD OF THE INVENTION

The present invention relates to a fluid dispensing system for establishing a fluid connection from one or more reservoirs of a fluid dispensing system towards a dosing device adapted to dispense the fluid to a patient, according to the preamble of the first claim. The present invention also relates to the use of such a reusable interconnection set for dispensing a fluid to a patient, in particular for dispensing a contrast fluid for CT scan or MRI scan to a patient. The present invention also relates to a fluid dispensing system comprising such a reusable interconnection set, to a fluid dispensing system comprising a reusable part and a disposable part and to the use of such a fluid dispensing system for dispensing a fluid to a patient, in particular for dispensing a contrast fluid for CT scan or MRI scan to a patient. The present invention also relates to a reusable interconnection set for use in such a dispensing system.

DESCRIPTION OF RELATED ART

Contrast medium dispensing systems are well known in the art. The known dispensing systems usually comprise a spike at one end for engaging a container which contains a stock volume of the contrast medium, and on the other end a mechanism with a luer connector for coupling the container to a manifold. A port of the manifold is coupled to a syringe adapted to administer fluid into the patient's vein. To reduce waste, many contrast medium dispensing systems include a temporary reservoir between the spike and the luer connector, to temporarily hold a quantity of contrast medium. In an effort to avoid cross contamination between patients, many systems include a reusable set carrying the spike and a disposable set carrying the connector providing the connection to the syringe, a pair of mating luer connectors for selectively joining the reusable and disposable set and a one way valve downstream the spike. By replacing the disposable set with each patient, one large container of contrast medium may be used with multiple patients.

An example of a contrast fluid dispensing system is disclosed in EP1726328. The fluid dispensing system comprises a disposable set with a first and a second tubing part which are releasable connectable to each other in a liquid tight manner, to permit carrying out a reflux control. The fluid connection between the first and second tubing part is established by means of a one-way valve which inhibits fluid flow from the patient in upstream direction, and thereby minimizes the risk for contamination of the fluid upstream the patient, which usually originates from a reservoir. The dispensing system further comprises means for delivering an amount of fluid originating from the reservoir, into the disposable set.

Another example of a contrast fluid dispensing system is disclosed in U.S. Pat. No. 6,800,072 B2. The dispensing system disclosed in U.S. Pat. No. 6,800,072 B2 comprises a tube with a first end connected to a spike adapted to be coupled in fluid communication to a bulk source of contrast medium. A second end of the tube comprises a first part of a luer connector which is provided to co-operate with a corresponding second part of the luer connector mounted to a disposable set. The disposable set comprises a reservoir which is in fluid connection with a further tubing which is adapted to conduct the contrast medium from the reservoir to a port of a manifold through a one-way valve. A syringe for delivering the contrast medium into the patients' vein is connected to an administering tubing which is connected to another port of the manifold. The reservoir comprises a cap member which is adapted to reduce the risk to splattering and the ensuing formation of bubbles in the reservoir.

When analyzing existing systems, the inventor realized that the replacement of individual packages of contrast fluid containing the dose for a single patient by a bulk container which contains multiple doses of contrast fluid and is capable of serving multiple patients, was made possible by the dispensing system disclosed in EP 1726328. The one way valve present in the dispensing system disclosed in EP 1726328 inhibits back flow of fluid from the patient to the bulk container and thereby prevents contamination of the bulk container by the patient. This replacement of small individual volumes by a bulk container permitted to reduce waste of contrast fluid, as flushing operations could be reduced to a minimum.

The inventor has however observed that the use of a bulk container for administering contrast medium to multiple patients introduced another problem which did not occur to an observable extent when using individual volumes of contrast fluid. When using a bulk container of contrast fluid, usually the required amount of fluid to be injected into a patient is extracted from the bulk container, and measured using a filling chamber of a predefined volume in which a piston is slidably moveable to draw the required fluid volume from the bulk container into the filling chamber and to forward the fluid towards the patient under pressure. The filling chamber usually forms part of an injection set. To seal the filling chamber and prevent fluid from leaking along the piston, the piston is surrounded by a plastic ring or joint. Reusing the same filling chamber for multiple patients instead of limiting it to one single patient, overcomes the need of flushing with contrast fluid, saving the cost and time for flushing the injection set with contract fluid and for the replacement of the injection set for every patient. A disadvantage however is that because of the prolonged use the moving parts of the filling chamber, in particular the joint surrounding the piston, are subject to wearing, whereby particles which originate from the filling chamber may be released into the fluid. Although the contrast fluid to be injected is usually of a very high purity, this wearing results in the occurrence of unwanted particles in the filling chamber and in the fluid to be injected into the patient. This problem cannot simply solved by regularly flushing the injection set. Moreover, regularly flushing the injection set would result in an important waste of contrast fluid which is very expensive.

Another particular problem when using a bulk container of contrast fluid is the increased risk to the occurrence of crystallization in the contrast fluid contained in the bulk container and the formation of crystals, as the bulk container is typically in use for a longer period of time than an individual package due to its larger volume. The phenomenon of the occurrence of crystallisation in a contrast fluid is known in the art, but it has not presented problems when individual packages of contrast fluid were used, because these packages were typically only opened shortly before actual use.

The administering of particles as described above, e.g. glass, rubber or grown crystals etc, even in very small quantity or size is to be avoided, as they can cause serious health problems to a patient, and can even lead to the death of the patient.

Once the inventors had realized the problems above, the solution of inserting into the fluid dispensing system, a filter for removing particles was immediately clear. It shall be clear that within the scope of the present invention the wording "particle" or "particles" refers to solid material particles.

BRIEF SUMMARY OF THE INVENTION

It is therefore an object of the present invention to provide a fluid dispensing system for dispensing one or more fluids into a patient, in such a way that the risk of unwanted particles being injected into the patient is minimized.

This problem is solved by a fluid dispensing system showing the technical features of the characterizing part of the first claim.

Thereto, the fluid dispensing system of this invention is characterized in that the fluid dispensing system comprises a first particle filter for preventing particles of a size larger than a predetermined first size from being injected into the patient, the first particle filter being located downstream the one or more chambers.

By providing a fluid dispensing system having such a particle filter, located downstream the one or more chambers, unwanted particles such as glass or rubber particles originating from the movable parts of the filling and injection set, or grown crystals originating from the contrast medium are blocked by the filter on the side of the reservoir, and thus prevented from being injected into the patient, thereby increasing the safety of a patient. The fluid dispensing system according to the invention allows the replacement of individual packages of contrast fluid containing the dose for a single patient by a bulk container containing contrast fluid for multiple patients, without intermediate flushing the reuse of the injection set for different patients with an increased safety of the patient and opens as a result the possibility of injecting more patients with contrast fluid per day.

In a preferred embodiment of the fluid dispensing system the first particle filter is inseparable embedded into the fluid dispensing system to avoid that the first particle filter needs to be manually connected by the personnel and minimize the risk of the first particle filter being forgotten or misconnected.

Preferably the one or more one way valves and the one or more second one way valves are inseparable embedded into the reusable interconnection set to minimize the risk of forgetting or misconnecting the first and second one way valves.

Preferably the first particle filter is located in the second tubing part downstream the filling and injection device, so that the first particle filter can be reused for several patients, thereby limiting the costs of the contrast fluid delivery system without decreasing the safety of the patients.

The present invention also relates to the use of the above described fluid dispensing set for dispensing a fluid to a patient, preferably into a patients' vein.

The present invention also relates to the use of the above described fluid dispensing set for dispensing a contrast fluid for CT scan or MRI scan to a patient, preferably into a patients' vein.

The invention is further elucidated in the attached figures and description of the figures.

LIST OF THE FIGURES

DETAILED DESCRIPTION OF THE INVENTION

Figure 1:
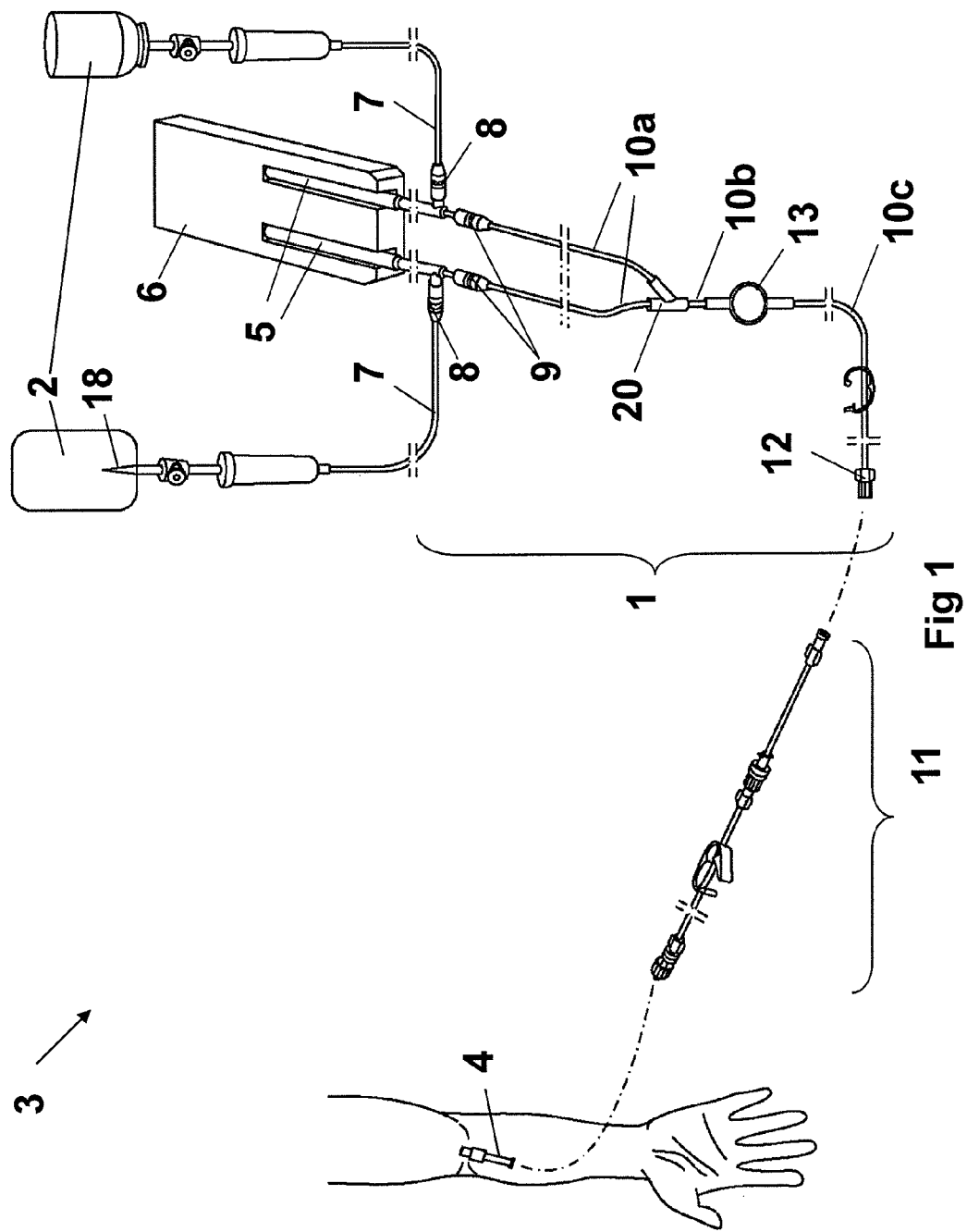
FIG. 1 shows a preferred embodiment of a fluid dispensing system according to the invention, comprising a disposable interconnection line, and a reusable interconnection set comprising a particle filter, which are releasable connectable to each other.

FIG. 1 shows an example of a fluid dispensing system according to the present invention.

FIG. 1 shows a fluid dispensing system 3 for dispensing one or more fluids from one or more reservoirs 2 towards a dosing device 4, the dosing device 4 being adapted to dispense the one or more fluids to a patient, in particular to a patients' vein. The fluid dispensing system 3 comprises a reusable interconnection set 1 suited for use with multiple patients. The reusable interconnection set 1 comprises for each reservoir 2: a first tubing part 7 for establishing a fluid connection from the reservoir 2 to a corresponding filling chamber 5 of a filling and injection device 6, each filling chamber 5 being provided for storing an amount of fluid from the corresponding reservoir 2; and a second tubing part 10 for establishing a fluid connection from each of the filling chambers 5 towards the dosing device 4, directly or indirectly via additional tubing. The fluid dispensing system 3 further comprises a first particle filter 13 for preventing particles of a size larger than a predetermined first size from being injected into the patient. According to the invention, the first particle filter 13 is located downstream of the filling chambers 5.

With fluid dispensing system 3 is meant a simple system such as the reusable interconnection set 1 itself, but can also mean a more complex system such as the whole system shown in FIG. 1, including the reservoirs 2 and the filling and injection device 6.

Corresponding first and second tubing parts 7, 10 can be routed separately to the filling chamber 5, or can be connected together before being routed to the filling chamber 5. The latter is preferred because in that case only one connection with the filling chamber 5 is required.

The purpose of the filling and injection device 6 is to facilitate injection of a specific amount of fluid, e.g. contrast media, at the proper time and under the proper pressure to the patient. The filling chambers 5 are provided for storing the predetermined amount of fluid from the corresponding reservoirs 2. This amount may be constant for all fluids and all patients, or may vary per fluid or per patient, and can e.g. depend on the size or weight of the patient.

The second tubing part 10 can have multiple segments 10a, 10b, 10c, which are fluidly connected to each other, and which are jointly referred to as "the second tubing part".

As a dosing device 4 any suitable device known to a person skilled in the art may be used. A suitable example of a dosing device is a syringe or injection needle.

In FIG. 1, the second tubing part 10 comprises a particle filter 13 for preventing unwanted particles, such as glass or rubber particles, or grown crystals of a contrast fluid, from being injected into a patient, in particular into a patients' vein, but according to the invention the particle filter can also be located further downstream. Without the particle filter 13 these particles could be transported via the blood vessels over the entire human body, even towards the hart and brain, where even very small particles can cause serious health problems to the patient. Thus by the addition of a particle filter 13 to the above described fluid dispensing system 3 the safety of the patient is largely increased. The inventor has found that there are three main causes of the occurrence of such particles. A first cause originates from the contact of a needle or spike with a glass or ceramic container. A second cause is wear of moving parts, e.g. rubber parts, in the filling chamber 5 of the filling and injection system 6. A third cause is growing crystals in the contrast fluid. The risk of occurrence of grown crystals is higher with a larger reservoir 2 of contrast fluid, as a larger reservoir is typically connected for a longer time period, thus the risk for contact with air is increased, giving the crystals more time to grow. The fluid dispensing system 3 of the present invention is therefore extremely useful to prevent accidents in hospitals where during a certain time period, e.g. a weekend, no CT or MRI scans are performed, or where the reservoir of contrast fluid is not renewed frequently enough. Knowing that the price of contrast medium is very high, the addition of a particle filter 13 can help to slightly extend the use of a reservoir 2 with contrast fluid in a safe manner, thus leading to cost reductions.

The particle filter 13 can have a circular shape, as shown in FIG. 1, or a rectangular shape, or any other shape found useful by the person skilled in the art.

The tubing of the first tubing part 7 and the second tubing part 10 can be made of any suitable material known to the person skilled in the art. However, when used to dispense contrast fluid, it is preferably made of a flexible plastic material which can be safely used with the fluid inside, for example polyvinylchloride. The dimensions (e.g. length, inner diameter, outer diameter, etc) of the first and second tubing part 7, 10 are not critical to the present invention and may be adapted by the person skilled in the art to the intended application. In CT scan systems the distance and thus the length of the tubing between the injection needle 4 and the reservoir 2 containing the contrast medium will often be approximately 1 meter. Such a tubing usually has an internal volume of approximately 7-8 ml, the over-all content of the contrast fluid being approximately 110 ml, and the pressure used to inject the fluid typically being 2 MPa, which is about 300 psi. However, with MRI imaging often the fluid is injected into the patients' vein under a higher pressure of e.g. 8 MPa, which is about 1200 psi, and a somewhat larger distance may need to be bridged. To minimize the risk to local expansion of the tubing, usually use will be made of tubing having a relatively thicker material thickness. As in MR imaging the contrast fluid volume is often limited to 10-15 ml, usually use will be made of a tubing having a smaller internal diameter and an internal volume of only approximately 3 ml, although this may be somewhat more or somewhat less. A commonly used length of tubing in MR imaging is approximately 120 cm, although this may be longer or shorter depending on the nature of the device used.

As shown in FIG. 1 each reservoir 2 is typically connected to the first tubing part 7 via a flow regulator in the form of a drip chamber for controlling the rate of fluid flow from the bag or bottle into the chamber and to the patient, but the drip chambers are not essential for the present invention.

The fluid dispensing system 3 shown in FIG. 1 has two reservoirs 2, e.g. one containing a contrast fluid, and the other containing a physiologic fluid, but the present invention will also work for a fluid dispensing system 3 with only one reservoir 2, or more than two reservoirs 2. The reservoir 2 can e.g. be a glass bottle or a plastic bag, or any other container found suitable by the person skilled in the art.

As in the example of FIG. 1 two reservoirs 2 are used, the second tubing parts 10a are connected to an inlet of a manifold 20, wherein the fluids from the two filling chambers 5 are mixed. In this document the manifold 20 is considered part of the second tubing part 10, as its function is merely to conduct fluids. The outlet of the manifold 20 is fluidly connected to an outlet connector 12 of the reusable interconnection set 1. The manifold 20 used in FIG. 1 is a Y-connection, but it could also be a T-connection, or any other suitable connection known to the person skilled in the art. The manifold 20 can be mounted somewhere centrally of the second tubing part 10, or be shifted to one of its ends. The manifold 20 can also be integrated in the outlet connector 12.

Preferably each first tubing part 7 comprises a first one way valve 8 oriented in such a way that in use the fluid is allowed to flow from the reservoir 2 to the filling chamber 5, but is prevented to flow in the opposite direction.

Preferably each second tubing part 10 comprises a second one way valve 9 oriented in such a way that in use the fluid is allowed to flow from the filling chamber 5 towards the dosing device 4 but is prevented to flow in the opposite direction.

Within the scope of the present invention, any one way valve considered suitable by the person skilled in the art may be used. The first one way valve 8 may be mounted somewhere centrally of the first tubing part 7, or be shifted to one of its ends. The second one way valve 9 may be mounted somewhere centrally of the second tubing part 10, or be shifted to one of its ends.

The way of connecting each filling chamber 5 to the first tubing part 7 comprising a first one way valve 8 and to a second tubing part 10 comprising a second one way valve 9 ensures that when the moving part (not shown) in the filling chamber 5 is moved inwards into the chamber 5, liquid is drawn from the reservoir 2 through the first tubing part 7 and through the first one way valve 8 which is open, while the second one way valve 9 is closed. When the moving part in the filling chamber 5 is moved outwards of the chamber, liquid in the filling chamber 5 is ejected through the second one way valve 9 into the second tubing part 10 towards the outlet connector 12, while the first one way valve 8 is closed.

It is essential for the present invention that the at least one particle filter 13 is located in the path of the fluid between the filling chambers 5 and the dosing device 4, in order to capture the envisioned particles. But several topologies are possible, as will be described further with reference to FIGS. 2-7, or any other configuration found useful by the person skilled in the art.

Preferably the first particle filter 13 is located in the second tubing part 10 of the reusable interconnection set 1 downstream the filling chambers 5.

Preferably the first particle filter 13 is inseparable embedded into the fluid dispensing system 3. Preferably also the first one way valves 8 and the second one way valves 9 are inseparable embedded into the fluid dispensing system 3. Preferably also the at least one particle filter 13 is inseparable embedded into the fluid dispensing system 3. This can be done with techniques such as glueing or welding or any other technique known to the person skilled in the art. By providing a complete interconnection set 1 or system 3 with embedded first one way valve(s) 8 and second one way valve(s) 9 and particle filter(s) 13, handling by medical personnel can be reduced to a minimum, thereby saving time and reducing the risk of misconnections or forgetting parts to a minimum. This embedding is particularly useful when the fluid dispensing system 3 is nothing more than the reusable interconnection set 1 itself.

Preferably the at least one particle filter 13 is chosen in such a way that the largest allowed particles of the contrast medium for CT scan or an MRI scan can pass through, but larger particles are blocked. Particle filters 13 are known in the art. Ideally the particle filter should be chosen depending on the particle size of the particles present in the liquid to be injected into the patient, and those to be prevented to be injected into the patient. The size of the particles of a contrast fluid is usually not an exact single size but has a certain distribution with an average value and a standard deviation. The person skilled in the art can e.g. choose a particle filter 13 that blocks particles having a size larger than an average size+N times the standard deviation, where N is e.g. chosen equal to 3 or 4 or 5 or 6 or 10 or any other number found useful by the person skilled in the art. The higher the number N, the larger the size of the particles that can pass, and the longer it will take before the particle filter 13 is blocked with unwanted particles. The person skilled in the art should also consider the pressure drop caused by the particle filter 13. For example, he could choose a filter that does not cause a pressure drop larger than 0.2 MPa. If so desired, multiple particle filters 13 can be placed in parallel to decrease the pressure drop.

Preferably the first size is a size larger than 2 μm, preferably larger than 1 μm, more preferably larger than 0.5 μm.

As a specific example, if a contrast fluid is used having particles with an average particle size of 1.0 μm and the distribution of the particles has a standard deviation of 10%, a particle filter 13 that blocks particles having a size of 1.5 μm could be chosen. By choosing a particle filter 13 with a smaller mesh, smaller unwanted glass or rubber particles would also be stopped, but the risk of the filter becoming blocked, or the pressure drop becoming too large would also increase. The person skilled in the art should make a good tradeoff taking into account the number of intended reuses of the reusable interconnection set 1. As an example, it might be a good strategy to replace the reusable interconnection set 1 at least every morning.

Optionally the reusable interconnection set 1 of the fluid dispensing system 3 can comprises a second particle filter for blocking particles of a much larger size than the average size of the particles in the container 2, e.g. to block particles larger than 100 μm, preferably larger than 50 μm, more preferably larger than 20 μm, most preferable larger than 10 μm. Such a particle filter would have the advantage of still blocking relatively large particles, while causing only minor pressure drop. The main purpose of the second particle filter would be to lower the risk of the first particle filter 13 becoming blocked.

Preferably the fluid dispensing system 3 of the present invention comprises an outlet connector 12 to enable a releasable connection with the dosing device 4, or to enable connection of additional tubing. Preferably the outlet connector 12 of the reusable interconnection set 1 is a Luer connector. A Luer connector is well known in the art, and provides good interconnection means with other parts such as the disposable interconnection part 11. However, the use of a Luer connector is not essential to the invention, and any other connection means that is releasable and liquid tight known to the person skilled in the art can also be used, for example any type of connector with internal or external threading.

Optionally the fluid dispensing system 3 comprises a disposable interconnection line 11 intended to be renewed with each patient; the disposable interconnection line 11 providing a fluid connection between the reusable interconnection set 10 and the dosing device 4.

In the context of the present invention, the disposable interconnection line 11 is located proximal to the patient, and the reusable interconnection set 1 is located distal from the patient. Within the reusable interconnection set 1 the first tubing part 7 is located distal from the patient and the second tubing part 10 is located proximal to the patient.

Preferably the reusable interconnection set 1 and the disposable interconnection line 11 are foreseen to be in fluid connection with each other by means of a releasable connection device 12. This connection device 12 can be made of any suitable connector which permits to releasably connect two parts of a tubing in a liquid tight manner, for example a luer connector or a bayonet coupling or any other coupling known to the person skilled in the art.

Preferably the reusable interconnection set 1 of the fluid dispensing system 3 of the present invention is in direct connection with the disposable interconnection line 11, without intermediate devices or instruments, apart from mere additional length of tubing with connectors at both ends, but the invention is not limited thereto.

The primary function of the disposable interconnection line 11 is to fluidly connect the reusable interconnection set 1 of the fluid dispensing system 3 to the dosing device 4, but it can have additional elements that offer particular advantages, such as the disposable interconnection line 11 disclosed in EP1726328, which allows to perform a reflux control and is foreseen to prevent contamination upstream towards the reusable interconnection set 1 and beyond. However, the use of that specific disposable interconnection line 11 is not required for the present invention, and any other suitable fluid connection line 11 known to the person skilled in the art can also be used. In the context of the present invention, any additional interconnection line between the reservoirs 2 and the dosing device 4 belongs to either the disposable interconnection set 11, when it is renewed with each patient, or to the reusable interconnection set 1, which is reused for at least two patients.

In an alternative embodiment of the fluid dispensing system 3 of the present invention, the first particle filter 13 is located in the disposable interconnection line 11, although this solution is less economic, as the disposable interconnection set 11 is renewed with each patient.

Preferably the fluid dispensing system 3 of the present invention is capable of withstanding a fluid pressure up to 2 MPa, preferably up to 8 MPa. 2 MPa is a maximum pressure used for injecting a contrast fluid for CT scan, and 8 MPa is a maximum pressure used for injecting a contrast fluid for MRI scan.

The present invention also relates to the use of such a fluid dispensing system 3 for dispensing one or more fluids to a patient, e.g. into a patients' vein.

The present invention also relates to the use of such a fluid dispensing system 3 for dispensing a contrast fluid for CT scan or MRI scan to a patient, e.g. into a patients' vein.

The present invention also relates to a reusable interconnection set 1 for use in a fluid dispensing system 3 as described above, wherein the reusable interconnection set 1 comprises the first particle filter 13, as described above.

The present invention also relates to a reusable interconnection set 1 for dispensing one or more fluids from one or more reservoirs 2 towards a dosing device 4, the dosing device 4 being adapted to dispense the one or more fluids to a patient, wherein the reusable interconnection set 1 essentially consists of: one or more first tubing parts 7 for establishing a fluid connection from the one or more reservoirs 2 to corresponding filling chambers 5 of a filling and injection device 6, each filling chamber 5 being provided for storing an amount of fluid from the corresponding reservoir 2, each first tubing part 7 having a first one way valve 8 oriented in such a way that in use the fluid is allowed to flow from the reservoir 2 to the filling chamber 5 but is prevented to flow in the opposite direction; and first connection means 21 located at the inlet of the one or more first tubing parts 7 for establishing a liquid tight connection with the one or more reservoir 2; and one or more second tubing parts 10 for establishing a fluid connection from the filling chambers 5 towards the dosing device 4, each second tubing part 10 having a second one way valve 9 oriented in such a way that in use the fluid is allowed to flow from the filling chamber 5 towards the dosing device 4 but is prevented to flow in the opposite direction; and second connection means 22 located at the inlet of the one or more second tubing parts 10 for establishing a liquid tight connection with the corresponding filling chambers 5; and outlet connection means 12 located downstream the one or more second one way valves 9 to enable attachment of external tubing towards the dosing device 4; and at least one particle filter 13 for preventing particles of a size larger than a predetermined size from being injected into the patient, the at least one particle filter 13 being located in the one or more second tubing parts 10. This interconnection set 1 is essentially a subset of the fluid dispensing system 3 as shown in FIG. 1. The first connection means, the second connection means, and the output connection means can e.g. be a male or female connector, or a length or tubing, or any other connection means found useful by the person skilled in the art.

The reusable interconnection set 1 of the present invention is suitable for use with any fluid dispensing system 3 for dispensing a fluid to a patient. The reusable interconnection set 1 of this invention is particularly suitable for dispensing a fluid to a patients' vein, more particularly for dispensing contrast fluid into a patients' vein. However, the reusable interconnection set 1 of the present invention is suitable for dispensing any fluid to a patient and into a vein of a patient. It is for example suitable for use with pain pumps or dialysis devices.

Preferably the first one way valves 8 and the second one way valves 8 and the particle filter 13 of this reusable interconnection set 1 are integrated in a single housing. In this case the first tubing parts and second tubing parts can for example be channels inside the housing.

The present invention also relates to the use of such a reusable interconnection set 1 for dispensing one or more fluids to a patient.

The present invention also relates to the use of such a reusable interconnection set 1 for dispensing a contrast fluid for CT scan or MRI scan to a patient.

FIGS. 2-7 show several examples of a reusable interconnection set 1 according to the present invention, but the invention is not limited thereto. Their structure and working is based on the same principles as described above, but vary e.g. in the number of reservoirs 2, or the location of the one or more particle filters 13. Other variations than the ones shown in FIGS. 2-7 are also possible, such as e.g. a reusable interconnection set 1 foreseen to connect three or four or any number of reservoirs 2, or having multiple particle filters 13 connected in series and/or in parallel, or the particle filter 13 being located "before" the second one way valve 9 or "behind" the second one way valve 9 when looking in the streaming direction of the fluid, or by choosing other types of connector(s), etc. It is clear from FIG. 1 and FIG. 2 how such reusable interconnection sets 1 can be used in a fluid dispensing system 3 according to the invention, such as the one shown in FIG. 1.

Figure 2:
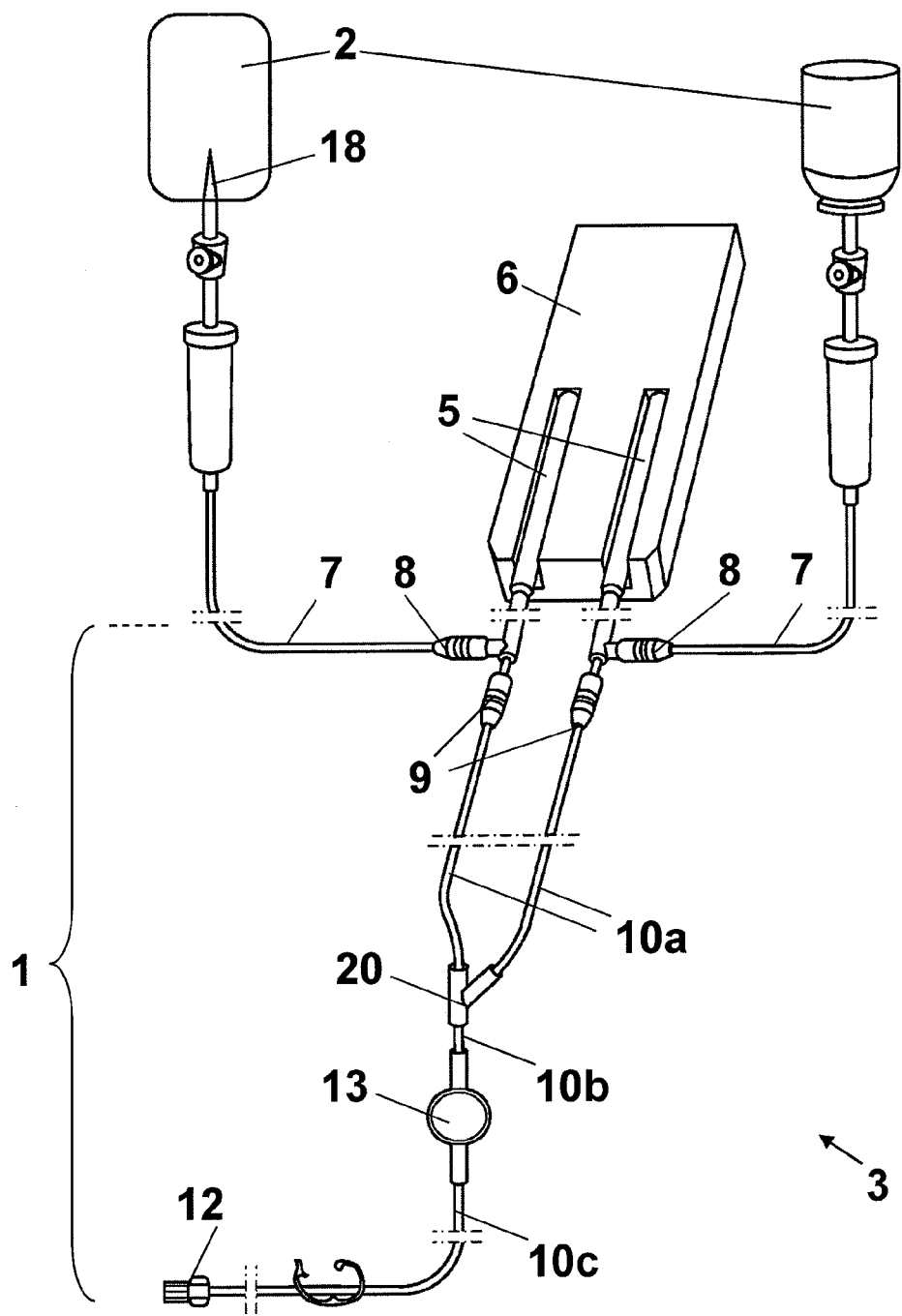
FIG. 2 shows the preferred embodiment of a reusable interconnection set according to the present invention intended for the connection of two reservoirs and a filling and injection device with two chambers to a dosing device.

FIG. 2 shows the preferred embodiment of a reusable interconnection set 1 with two containers 2, according to the present invention. Note that in this configuration only one particle filter 13 is required, independent of the number of reservoirs 2, and a mix of all liquids passes through this single particle filter 13. As the elements and the working of this interconnection set 1 is already described above, FIG. 2 needs no further explanation. This configuration has a price advantage over the configurations shown in FIG. 3 and FIG. 4 to be discussed next.

Figure 3:
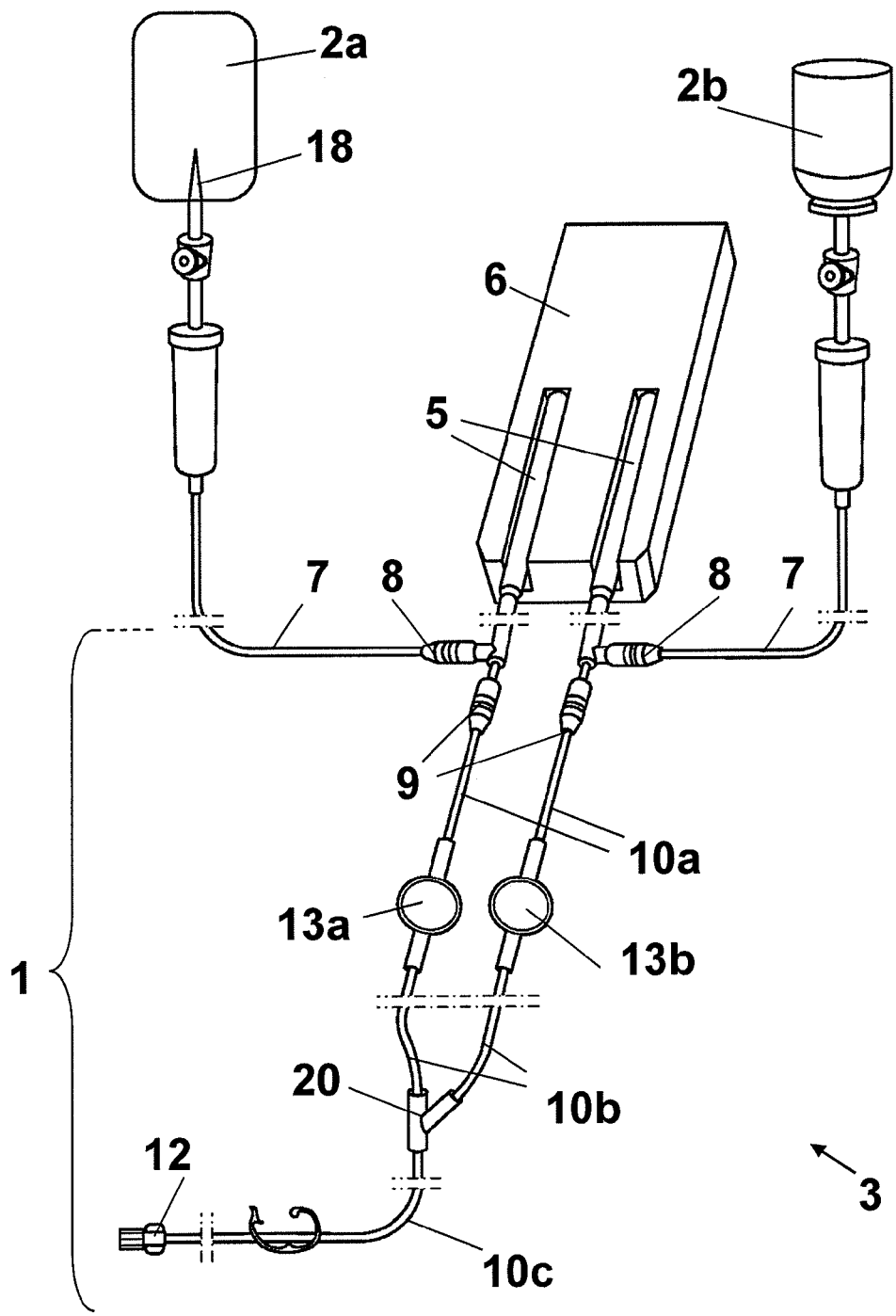
FIGS. 3 and 4 show an embodiment of a reusable interconnection set according to the present invention intended for the connection to two reservoirs and a filling and injection device with two chambers, with different positions of the particle filters and the one-way valves, to a dosing device.

FIG. 3 shows a variation of the reusable interconnection set 1 of FIG. 2, whereby the reusable interconnection set 1 has two particle filters 13, one for each reservoir 2. This configuration has the advantage that the characteristics of each particle filter 13 can be optimized to the characteristics of each liquid. For example, if the particles of the liquid in the first reservoir 2a have a larger diameter than the particles of the liquid in the second reservoir 2b, the particle filter 13b corresponding to the second reservoir 2b can be adopted to stop unwanted particles of a smaller size than the particle filter 13a guiding the fluid of the first reservoir 2a.

Figure 4:
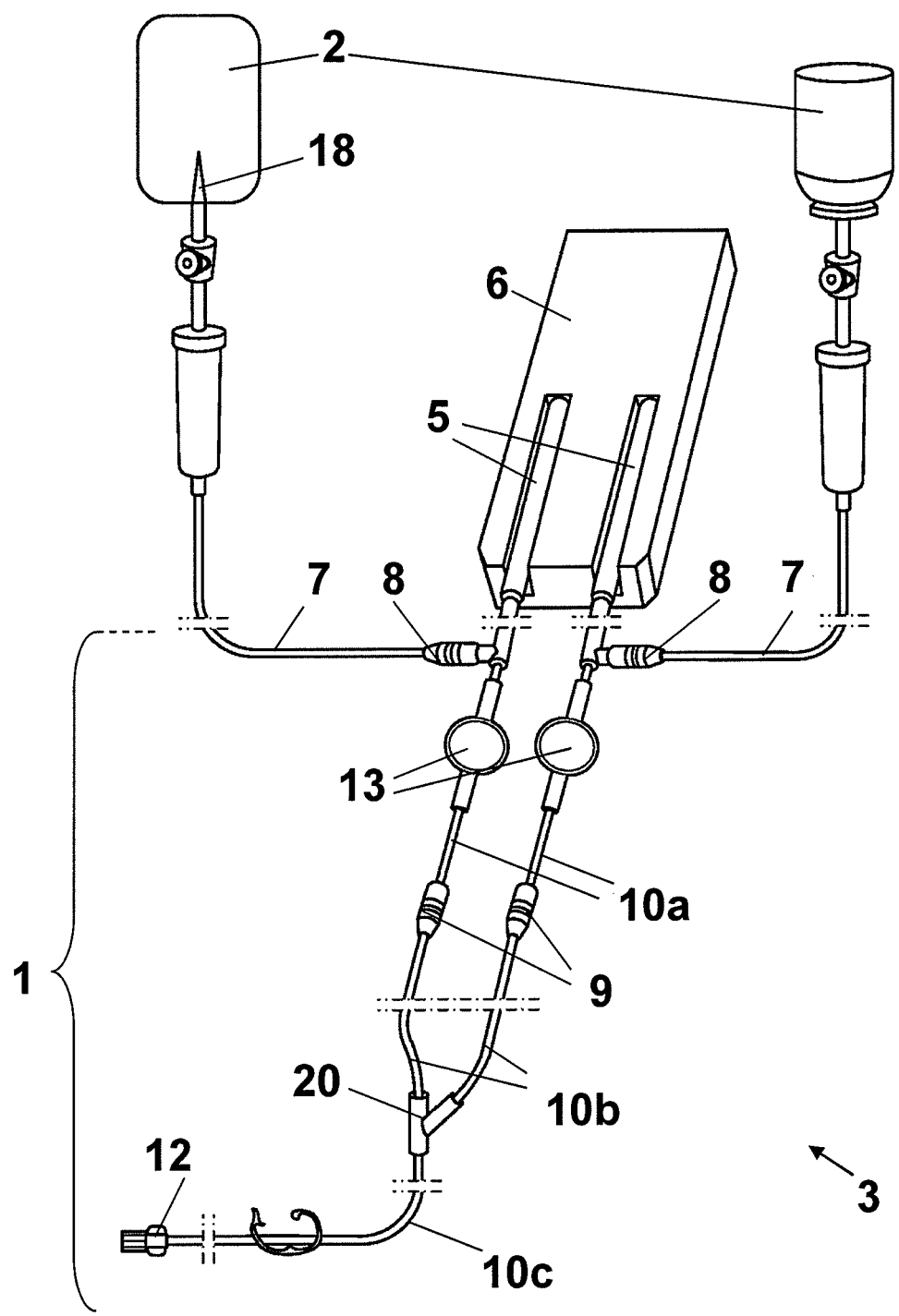

FIG. 4 shows a variation of the reusable interconnection set 1 of FIG. 3 according to the invention, whereby the position of the particle filters 13 and the second one way valves 9 are swapped. An advantage of the configuration of FIG. 4 over that of FIG. 3 is that the risk of the mechanism of the second one way valves 9 being blocked by unwanted particles is reduced, since the particles would already be stopped before reaching the second one way valves 9. This configuration thus provides a lower risk for back flow of the liquid, and thus of contamination of the filling chambers 5, and the fluid in the containers 2. In another variant (not shown), the topology of FIG. 3 is used for one fluid, and the topology of FIG. 4 is used for another fluid.

Figure 5:
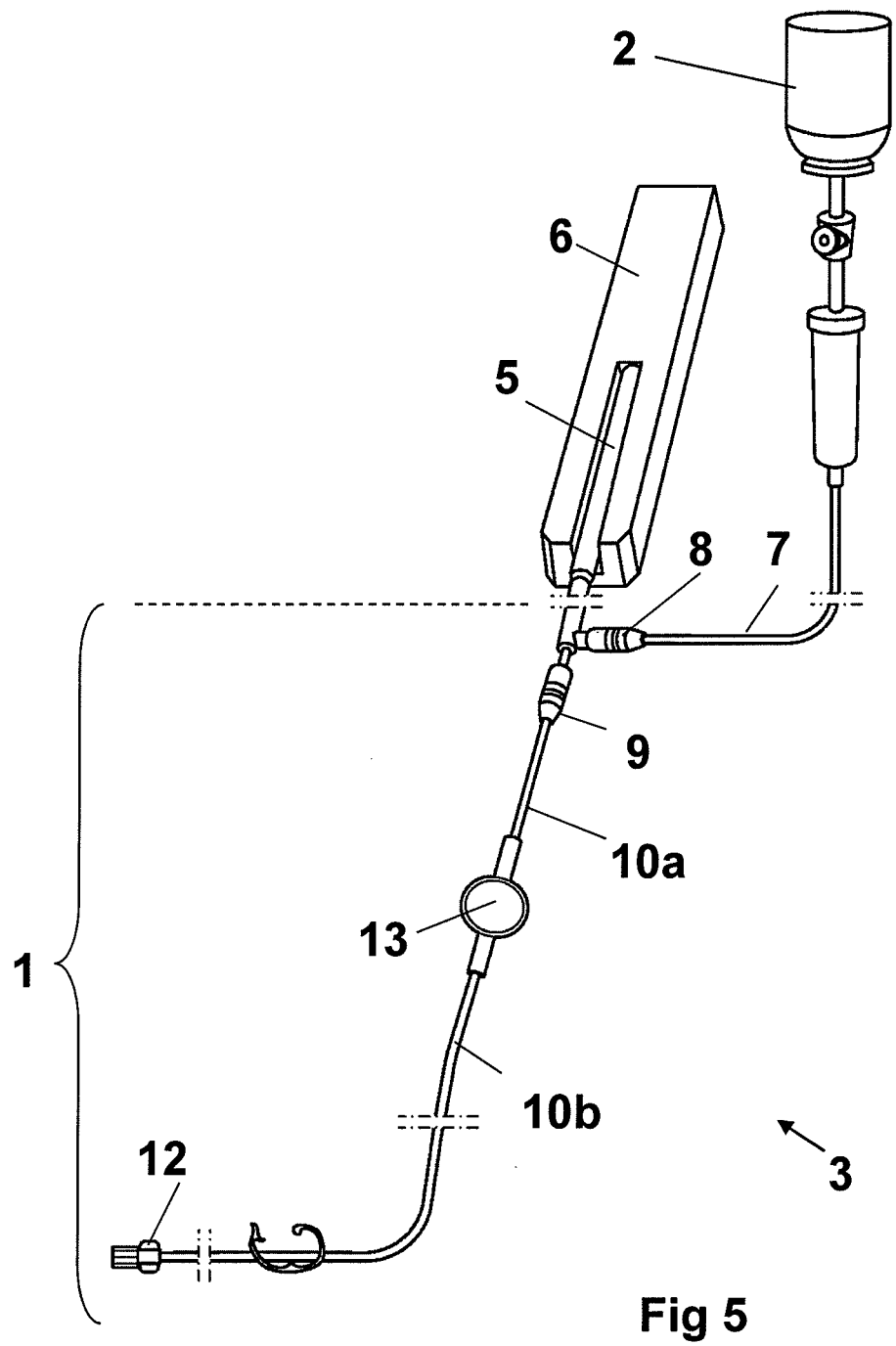
FIGS. 5 and 6 show an embodiment of a reusable interconnection set according to the present invention intended for the connection of one reservoir and a filling and injection device with one chamber, with different positions of the particle filters and the second one-way valve, to a dosing device.

FIG. 5 shows an example of a reusable interconnection set 1 according to the invention for dispensing a fluid from a single reservoir 2 to a patient. The configuration of this reusable interconnection set 1 is a subset of the one shown in FIG. 3, and it shares the same advantages as described above. In this configuration there is one particle filter 13, and it is located between the second one way valve 9 and the outlet connector 12.

Figure 6:
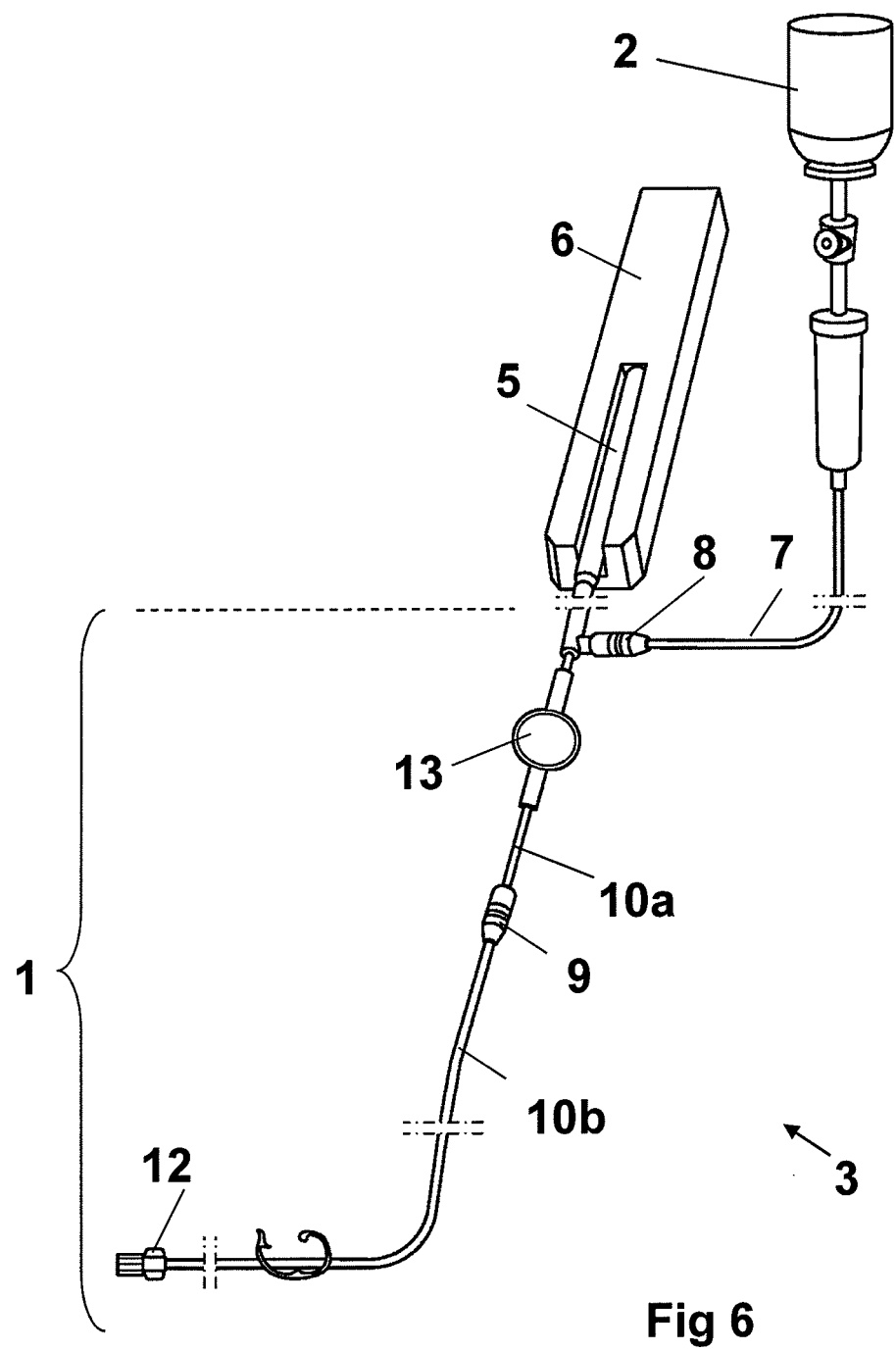

FIG. 6 shows a variant of the reusable interconnection set 1 of FIG. 5, whereby the position of the particle filter 13 and the second one way valve 9 are swapped. The configuration of this reusable interconnection set 1 is a subset of the one shown in FIG. 4, and it shares the same advantages as described above. In this configuration there is one particle filter 13, and it is located between the filling chamber 5 and the second one way valve 9.

Figure 7:
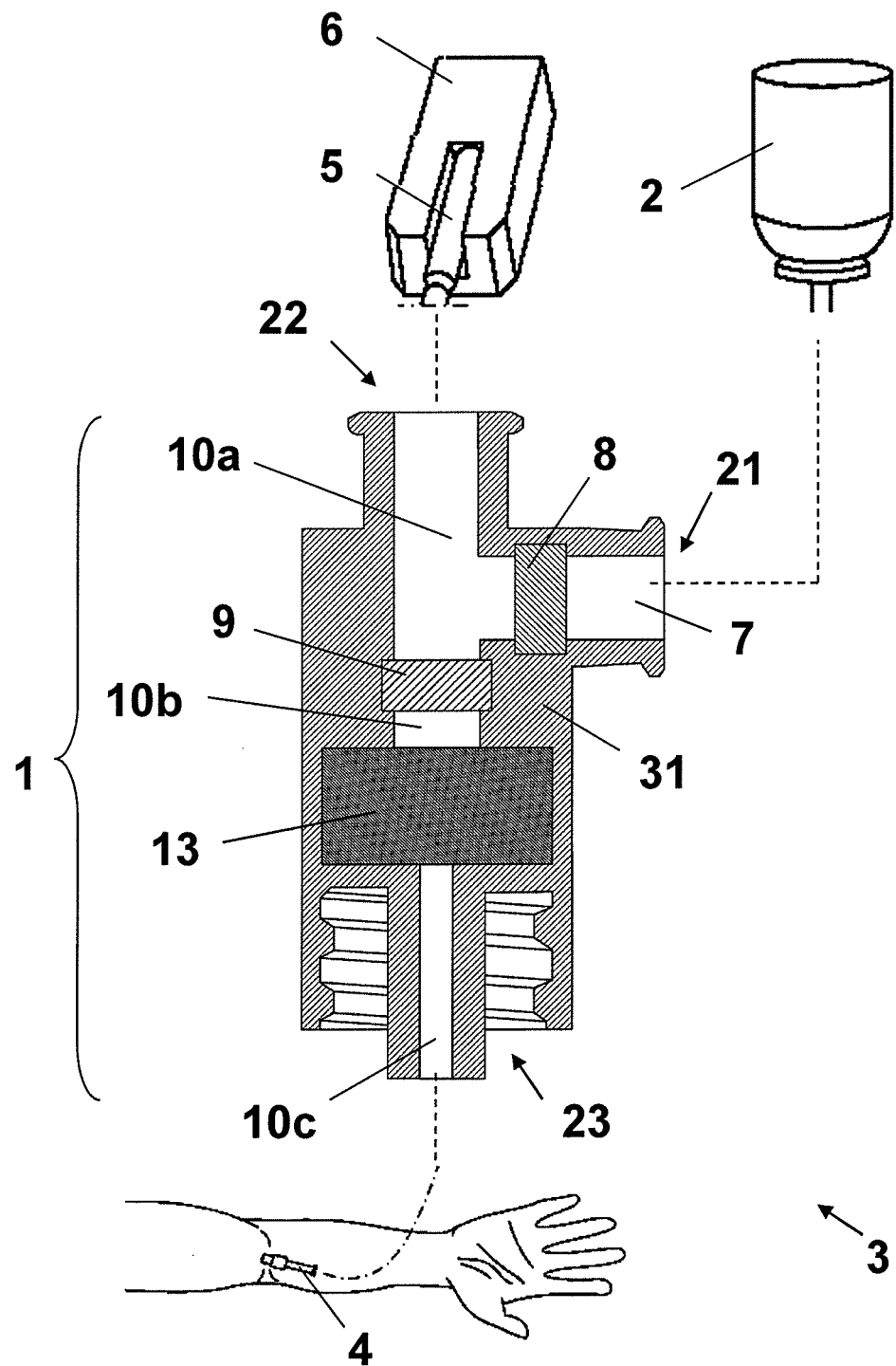
FIG. 7 shows a cross section of an integrated part that contains the first and second one way valve, and the particle filter, according to the present invention.

FIG. 7 shows an example of a highly integrated version of a reusable interconnection set 1 according to the invention. In the reusable interconnection set 1 shown in FIG. 7 the first one way valve 8, the second one way valve 9 and the particle filter 13 are integrated in a single housing or component 31. This integrated component 31 further comprises external thread at first inlet 21 to allow a liquid tight connection of the component 31 to the reservoir 2 via the first tubing part 7, and external thread at second inlet 22 to allow a liquid tight connection of the component 31 to the filling chamber 5 at a first end of the second tubing part 10, and internal thread at outlet 23 to allow a liquid tight connection of the component 31 and a disposable interconnection line 11. The integrated component 31 of FIG. 7 is functionally equivalent to the reusable interconnection set 1 shown in FIG. 5.

It is clear for the person skilled in the art that variants of this integrated component 31 can also be constructed for the reusable interconnection sets 1 shown in FIGS. 2-6. The highly integrated interconnection component 31 gives a cost advantage because the several components 8, 9, 13 can be placed in a single housing, and a storage advantage as the integrated interconnection component 31 is much more compact, thus requiring less space.

The integrated interconnection component 31 shown in FIG. 7 shows male and female Luer connectors, but other connectors known to the person skilled in the art can also be used, for example, instead of the external thread at the first and second inlet 21, 22 also an internal thread could be used, and instead of the internal thread at outlet 23 also external thread could be used. Instead of thread any other connection means known to the person skilled in the art could also be used, e.g. a length of tubing fixedly connected to the component 31, e.g. by glueing or welding or any other known connection means, or combinations thereof.

In another variant the integrated component 31 comprises a second particle filter, in a similar topology as described above for the fluid interconnection set 3, with the same advantages.

The invention claimed is:

1. A fluid dispensing system for dispensing one or more fluids from one or more reservoirs towards a dosing device, the dosing device being adapted to dispense the one or more fluids to a patient, the fluid dispensing system comprising
   a) a reusable interconnection set suited for use with multiple patients, the reusable interconnection set comprising for each reservoir:
      a first tubing part for establishing a fluid connection from the one or more reservoirs to a corresponding one or more filling chambers of a filling and injection device, each filling chamber being provided for storing an amount of fluid from the corresponding one or more reservoirs;
      a second tubing part for establishing a fluid connection from each of the filling chambers towards the dosing device; and
   b) a disposable interconnection line to be renewed with each patient; the disposable interconnection line providing a fluid connection between the reusable interconnection set and the dosing device, and comprising a first and a second tubing part which are releasable connectible to each other in a liquid tight manner, wherein a fluid connection between the first and the second tubing part is established by a one-way valve, wherein each first tubing part of the reusable interconnection set comprises one or more first one-way valves oriented in such a way that in use the amount of fluid is allowed to flow from the one or more reservoirs to the one or more filling chambers but is prevented to flow in the opposite direction;
   wherein each second tubing part of the reusable interconnection set comprises one or more second one-way valves oriented in such a way that in use the fluid is allowed to flow from the one or more filling chambers towards the dosing device but is prevented to flow in the opposite direction;
   wherein the fluid dispensing system comprises a first particle filter for preventing particles of a size larger than 0.5 μm from being injected into the patient, the first particle filter being located downstream of the one or more filling chambers within the second tubing part of the reusable interconnection set, and
   wherein the fluid dispensing system is configured to withstand a fluid pressure up to 2 MPa.

2. A fluid dispensing system according to claim 1, wherein the first particle filter is inseparable embedded into the fluid dispensing system.

3. A fluid dispensing system according to claim 1, wherein the one or more first one way valves and the one or more second one way valves are inseparable embedded into the fluid dispensing system.

4. A fluid dispensing system according to claim 1, wherein the fluid dispensing system comprises a second particle filter for blocking particles of a size larger than a second size, the second size being 100 μm, the second particle filter being located between the one or more filling chambers and the first particle filter.

5. A fluid dispensing system according to claim 4, wherein the second size is 50 μm.

6. A fluid dispensing system according to claim 4, wherein the second size is 20 μm.

7. A fluid dispensing system according to claim 1, wherein the fluid dispensing system comprises an outlet connector to enable a releasable connection with the dosing device.

8. A fluid dispensing system according to claim 1, wherein the first particle filter is located in the disposable interconnection line.

9. A fluid dispensing system according to claim 1, wherein the one or more first one-way valves, the one or more second one-way valves and the first particle filter are integrated in a single housing.

10. A fluid dispensing system according to claim 1, wherein the first size is a size larger than 1 μm.

11. A fluid dispensing system according to claim 1, wherein the first size is a size larger than 0.5 μm.

12. A fluid dispensing system according to claim 1, wherein the fluid dispensing system is configured to withstand a fluid pressure up to 8 MPa.

13. A reusable interconnection set for dispensing one or more fluids from one or more reservoirs towards a dosing device, the dosing device being adapted to dispense the one or more fluids to a patient, wherein the reusable interconnection set comprises:
   one or more first tubing parts for establishing a fluid connection from the one or more reservoirs to corresponding one or more filling chambers of a filling and injection device, each filling chamber being provided for storing an amount of fluid from the corresponding one or more reservoirs, each first tubing part having a first one way valve oriented in such a way that in use the fluid is allowed to flow from the one or more reservoirs to the one or more filling chambers but is prevented to flow in the opposite direction;

a first connector located at an inlet of the one or more first tubing parts for establishing a liquid tight connection with the one or more reservoirs;

one or more second tubing parts for establishing a fluid connection from the one or more filling chambers towards the dosing device, each second tubing part having a second one way valve oriented in such a way that in use the fluid is allowed to flow from the one or more filling chambers towards the dosing device but is prevented to flow in the opposite direction;

a second connector located at the inlet of the one or more second tubing parts for establishing a liquid tight connection with the corresponding one or more filling chambers;

an outlet connector located downstream the second one way valve to enable attachment of external tubing towards the dosing device;

wherein the reusable interconnection set has at least one particle filter for preventing particles of a size larger than a predetermined size from being injected into the patient, the at least one particle filter being located in the one or more second tubing parts.

14. A reusable interconnection set according to claim 13 wherein the first one way valve and the second one way valve and the at least one particle filter are integrated in a single housing.

15. Use of a reusable interconnection set according to claim 13 for dispensing one or more fluids to a patient.

* * * * *

UNITED STATES PATENT AND TRADEMARK OFFICE
CERTIFICATE OF CORRECTION

| | | |
|---|---|---|
| PATENT NO. | : 9,504,783 B2 | Page 1 of 1 |
| APPLICATION NO. | : 13/487845 | |
| DATED | : November 29, 2016 | |
| INVENTOR(S) | : Jean-Pierre Peters | |

It is certified that error appears in the above-identified patent and that said Letters Patent is hereby corrected as shown below:

In the Specification

Column 1, Line 46:
Delete "connectable" and insert --connectible--;

Column 5, Line 14:
Delete "hart" and insert --heart--;

Column 8, Line 19:
Delete "10" and insert --1--;

Column 9, Line 61:
Delete "8" and insert --9--.

Signed and Sealed this
Eleventh Day of April, 2017

Michelle K. Lee
*Director of the United States Patent and Trademark Office*